United States Patent [19]
Hsieh et al.

[11] Patent Number: 5,180,600
[45] Date of Patent: Jan. 19, 1993

[54] METHOD FOR DEEP-FAT FRYING FOOD PRODUCTS

[75] Inventors: Paonan Hsieh, Worthington; William T. McComis, Worthington; Nagabhusan Senapati, Worthington; Foster B. Stulen; Darrell D. Paul, both of Columbus, all of Ohio

[73] Assignee: Gas Research Institute, Chicago, Ill.

[21] Appl. No.: 674,208

[22] Filed: Mar. 25, 1991

[51] Int. Cl.$^5$ .............................................. A23L 1/00
[52] U.S. Cl. ................................... 426/233; 426/438
[58] Field of Search ...................... 426/231, 233, 438

[56] References Cited

U.S. PATENT DOCUMENTS 3,734,744  5/1973  Albright .............................. 426/438
4,372,980  2/1983  Luebke et al. ...................... 426/231

*Primary Examiner*—George Yeung
*Attorney, Agent, or Firm*—Watkins, Dunbar & Pollick

[57] ABSTRACT

Apparatus and methods are disclosed for cooking and indicating the doneness of food products immersed in a hot liquid cooking medium such as deep hot fat. An indicator circuit that cooperates with an acoustic detector produces a first control signal indicating that acoustic activity in the cooking medium has fallen to below a threshold level for a predetermined first period of time, and afterwards produces a second control signal correlated to the doneness of the cooked food product a predetermined second period of time following said predetermined first period of time.

6 Claims, 2 Drawing Sheets

METHOD FOR DEEP-FAT FRYING FOOD PRODUCTS

FIELD OF THE INVENTION

The present invention relates generally to apparatus for deep-fat frying certain foodstuffs, and particularly concerns fryer apparatus, and a method of fryer apparatus operation, for detecting the doneness of parfried potato segments and like foods cooked by immersion in hot cooking oil.

BACKGROUND OF THE INVENTION

Numerous different apparatus arrangements and methods of apparatus control are known for application to the cooking of certain foodstuffs such as parfried potato segments by immersion in hot cooking oil to obtain a desired or preferred degree of cooked product doneness. Such apparatus and methods have heretofore generally depended upon the sensing of hot cooking oil temperature levels for effectiveness.

U.S. Pat. No. 3,213,778 issued to Martino, for example, constantly senses cooking oil bath temperature and actuates a reversible electric motor to cause removal of the cooked product from the hot oil bath when a desired bath oil temperature has been attained.

U.S. Pat. No. 4,282,423 issued to Volz discloses a deep-fat fryer apparatus having a solid state control enabling operation of the apparatus in any one of several different modes, including a "cook" mode but apparently without attempting to establish degree of foodstuff doneness.

U.S. Pat. No. 4,362,094 issued to Polster discloses deep-fat fryer apparatus also having a solid state control but with a capability for determining rate of cooking in combination with detected elapsed time.

U.S. Pat. No. 4,503,320 also issued to Polster discloses an improved temperature-sensing probe utilized in deep-fat fryer apparatus to detect and integrate different hot-oil temperatures associated with different oil bath zones for cooking oil bath temperature control purposes.

Also, U.S. Pat. No. 4,812,625 issued to Ceste discloses a control arrangement for deep-fat fryer apparatus which facilitates operation of the apparatus in different modes including a cooking mode but without attempting to determine or detect cooked product doneness.

The above-identified prior art discloses the most relevant knowledge known to applicants regarding deep-fat frying apparatus and apparatus control for purposes of establishing cooked product doneness. Such prior art, if determining or detecting cooked product doneness, unnecessarily sense oil bath temperature levels to control an automatic cooking process. Improved deep-fat fryer cooking control advantages can be obtained automatically in fryer apparatus without having to detect and time cooking oil temperature conditions.

SUMMARY OF THE INVENTION

To achieve the objectives of the present invention we combine a conventional acoustic sensor with otherwise conventional deep-fat dryer apparatus and integrate that combination into a novel apparatus control that establishes a desired degree for cooked product doneness independently of hot-oil bath temperature and independently of cooked product initial temperature. The apparatus and method of this invention have proven particularly effective with respect to determining the doneness of deep-fried parfried potato segments, frozen or thawed. Also, the apparatus may be adapted, with variation, to the cooking of certain coated protein products such as breaded fish products or breaded poultry products.

The acoustic sensor utilized in this invention is preferably a conventional piezoelectric transducer which contacts the fryer apparatus hot-oil or oil bath container; alternatively the transducer device may be simply immersed in oil bath if appropriately protected. Such transducer detects any acoustic activity occurring within the hot oil bath during product cooking and generates a corresponding or correlated electrical output signal that is amplified, filtered, and detected when above a predetermined threshold level.

Doneness of the food product being cooked in the hot-oil bath is established as a function of a finite time period occurring after non-noise acoustic activity in the hot-oil bath ceases or is diminished to below a selected threshold level continuously throughout an initial control time period. In a preferred embodiment of the invention, the doneness of parfried potato segments being cooked in a hot-oil bath is deemed to occur at the end of a finite time period of approximately 85 seconds following an initial control period wherein transducer-detected acoustic activity drops below a pre-selected trigger level (e.g., to below 40 dB) for a relatively short time (e.g., 5 seconds) irrespective of variations in hot-oil actual temperature and irrespective of initial temperature of the parfried potato segments over relatively wide temperature ranges. At the end of the finite time period an appropriate alarm signal is generated by the apparatus.

The foregoing and other advantages of this invention will become apparent from the following disclosure in which preferred embodiments of the invention are described in detail and illustrated in the accompanying drawings. It is contemplated that variations in structural features and arrangement of parts may appear to the person skilled in the art, without departing from the scope or sacrificing any of the advantages of the invention.

DETAILED DESCRIPTION OF THE DRAWINGS

Figure 1:
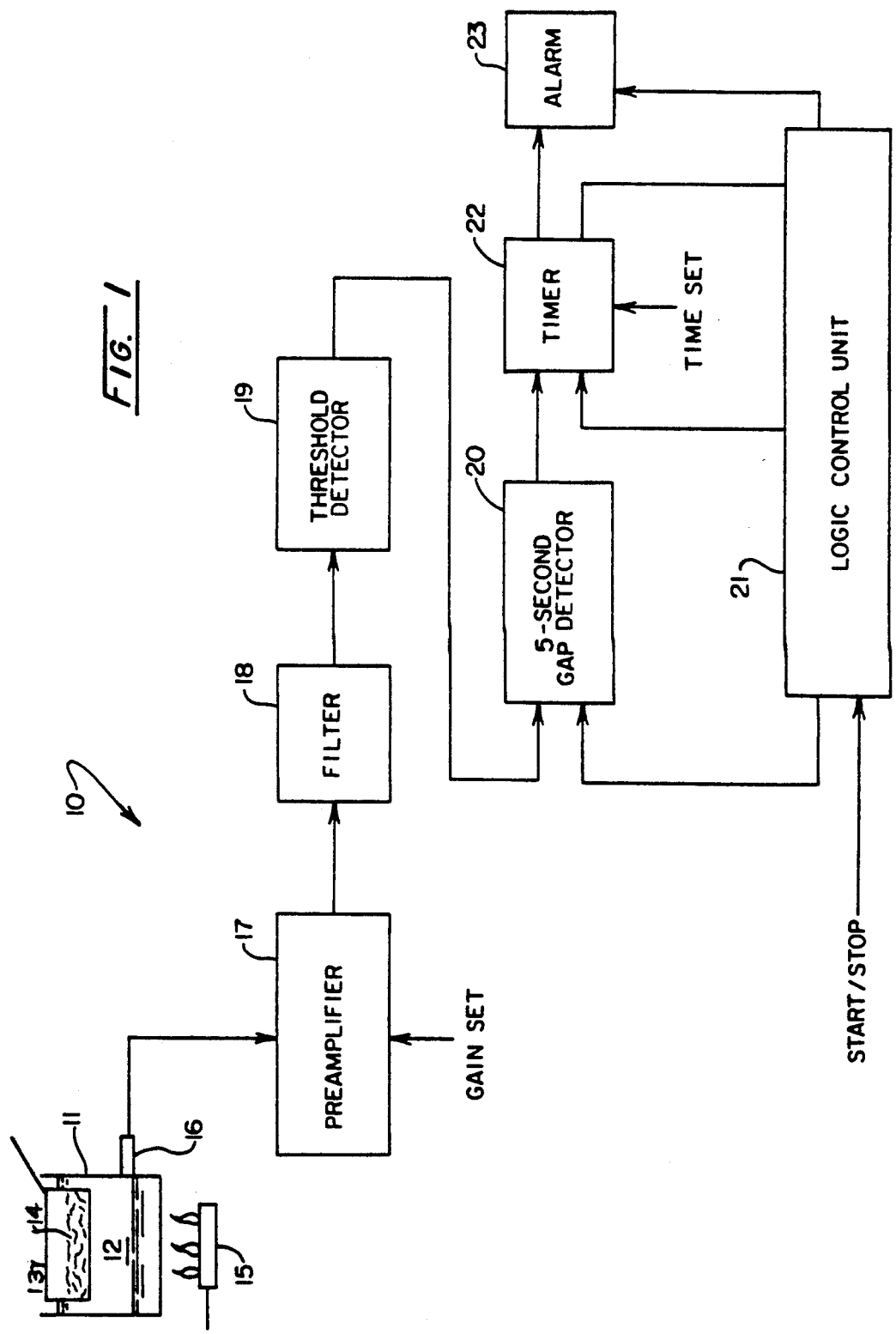
FIG. 1 is a schematic functional block diagram of control apparatus utilized in the practice of the present invention.

FIG. 1 schematically illustrated a preferred embodiment of the apparatus of our invention and such is designated generally by the reference numeral 10. Apparatus 10 includes a conventional deep-fat fryer oil bath container 11 which contains a hot-oil bath 12. A perforate basket 13 containing a batch of to-be-cooked food product 14 is partially placed within container 11 so that food product 14 is immersed in hot-oil bath 12 for cooking. Additionally, apparatus 10 is provided with a conventional gas burner assembly 15 that is thermostatically controlled and that functions to heat and control the temperature of hot-oil bath 12. A conventional thermostatically controlled electrical resistance element may be utilized in lieu of burner assembly 15.

As shown in FIG. 1, a conventional piezoelectric transducer 16 preferably contacts the exterior surface of container 11 and its output electrical signal is fed to the electronic preamplifier designated 17. In the event the maximum temperature of container 11 is excessive with respect to contact with transducer 16, it may be necessary to separate transducer 16 from direct contact with container by means of an intermediate acoustic wave guide. Also, transducer 16 if appropriately encapsulated, may alternatively be suitably immersed in hot-oil bath 12.

The electrical signals amplified at function 17 are next fed to filter 18 prior to utilization for control purposes. The filter pass band of filter 18 is chosen to exclude low-frequency noise produced by mechanical disturbances to container 11. A filter pass band frequency range of 30 kHz to 200 kHz is satisfactory for most deep-fat fryer applications. Threshold detector circuit 19 receives the filtered signal and detects those components of the transducer output signal having amplitude values above a pre-selected minimum signal amplitude (e.g., above 40 dB).

An acoustic gap detector circuit 20 is provided in control apparatus 10 to establish an initial control period reference from which the desired degree of food product doneness is established. Circuit 20 functions to detect a first minimum period of "silence" occurring in hot-oil bath 12 after food product 14 is immersed for cooking. For parfried potato segments and also for other food known food product cooking applications we detect the first 5-second acoustic gap or period of silence occurring at or above the acoustic signal trigger level established by threshold detector 19. The end of the detected gap or period of silence triggers timer circuit 22 which begins a fixed time period (e.g., 85 seconds) that follows the acoustic gap detected by gap detector 20. The end of the finite time period determined by timer circuit 22 produces an output signal that activates alarm 23. Alarm 23 may be an audible alarm or a visual alarm or both. It should be noted that circuits 20 and 22, as well as logic control circuit 21, may be designed, manufactured, and operated as conventional digital logic circuits having well-known AND and OR gate elements, clock pulse generators, pulse counters, and the like. Also, in designing deep-fat fryer apparatus for a variety of food product cooking applications it may be desirable to provide a capability for varying the time set incorporated into timer circuit 22. This normally would be accomplished by the use of logic control unit 21 which receives manual control inputs.

Controlled tests of the method of this invention were completed using nominal hot-oil bath temperatures in the range of 360°-375° F. for cooking parfried potato segments having either ⅛ inch × ⅛ inch or 3/16 inch by 5/16 inch cross sectional dimensions. Optimum cooking results were subjectively determined to involve approximately a 30% to 32% weight (moisture) loss for preferred cooked product color and texture. Consistently good results were obtained with an approximately 85 second alarm period following a 5 second "silence" period detected at gap detector circuit 20.

Figure 2:
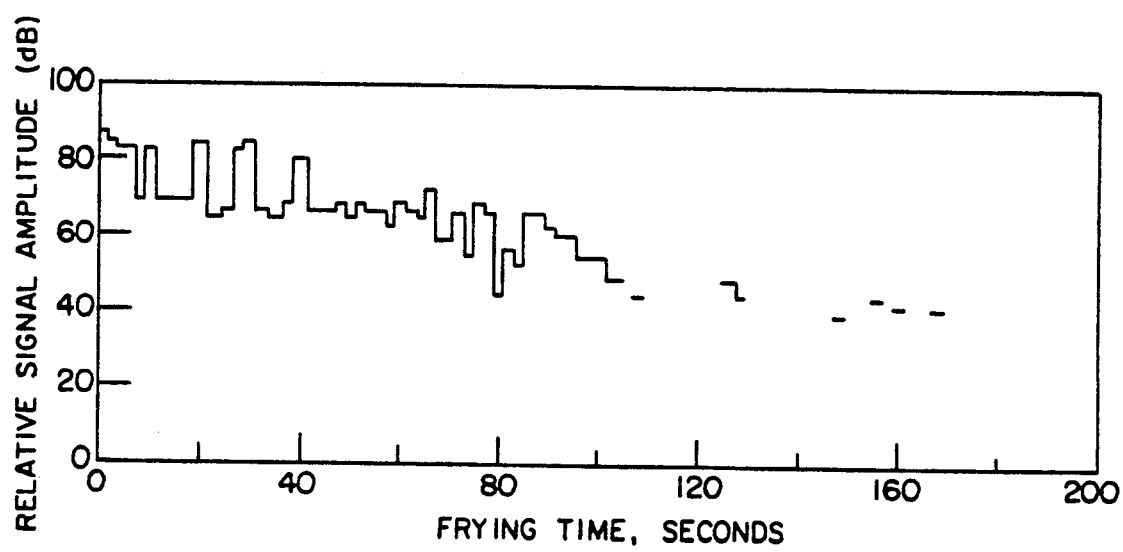
FIG. 2 is an acoustic amplitude plot as a function of time for a typical deep-fat cooking process for parfried potato segments.

FIG. 2 illustrates a representative plot of detected acoustic event activity above threshold as a function of time for the parfried potato deep-fat cooking process. As noted from that plot, the acoustic "silence" or gap commences at about the 110 second abscissa value. Doneness occurs afterwards at about the 200 second total time value. The selected doneness time value (e.g., 85 seconds following the detected 5-second period of silence) pertained for food product having either 0° F., 40° F., or 70° F. initial temperatures.

In the case of certain coated food products, e.g., breaded seafood sticks or breaded poultry patties, it will be necessary to utilize a control fixed time period different than the control fixed time period (e.g., 85 seconds) utilized for parfried potato segments.

It is herein understood that although the present invention has been specifically disclosed with the preferred embodiments and examples, modifications and variations of the concepts herein disclosed may be resorted to by those skilled in the art. Such modifications and variations are considered to be within the scope of the invention and appended claims.

What is claimed is:

1. A method of indicating the doneness of a food product immersed and cooked in a heated liquid oil medium comprising, the steps of;
   a) detecting acoustic activity occurring in the heated liquid medium and generating a correlated output electrical signal;
   b) detecting the amplitude of said correlated output electrical signal and generating a first control signal indicative of the correlated output signal having fallen below a predetermined threshold amplitude level continuously throughout a predetermined first period of time; and
   c) generating a second control signal at a predetermined second period of time following the generation of said first control signal, said second control signal being correlated to the doneness of the food product.

2. The method defined by claim 1 wherein said predetermined first period of time is in the range of approximately 3 to 8 seconds.

3. The method defined in claim 1 wherein said predetermined second period of time is in the range of approximately 50 seconds to 100 seconds.

4. The method defined by claim 1 wherein said predetermined second period of time is approximately 85 seconds.

5. The method defined by claim 2 wherein said predetermined second period of time is in the range of approximately 50 seconds to 100 seconds.

6. The method defined by claim 2 wherein said predetermined second period of time is approximately 85 seconds.

* * * * *